United States Patent
Belter

(10) Patent No.: US 12,304,878 B2
(45) Date of Patent: *May 20, 2025

(54) IRON SALT CATALYST REGENERATION

(71) Applicant: Randolph Belter, Zachary, LA (US)

(72) Inventor: Randolph Belter, Zachary, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/507,882

(22) Filed: Nov. 13, 2023

(65) Prior Publication Data
US 2024/0150266 A1    May 9, 2024

Related U.S. Application Data

(63) Continuation-in-part of application No. 18/049,211, filed on Oct. 24, 2022, now Pat. No. 12,091,376.

(51) Int. Cl.
| | | |
|---|---|---|
| *C07C 17/02* | (2006.01) | |
| *B01J 31/16* | (2006.01) | |
| *B01J 37/04* | (2006.01) | |

(52) U.S. Cl.
CPC ........... *C07C 17/02* (2013.01); *B01J 31/1616* (2013.01); *B01J 37/04* (2013.01); *B01J 2231/4205* (2013.01); *B01J 2531/842* (2013.01)

(58) Field of Classification Search
CPC ... C07C 17/281; B01J 27/128; B01J 31/0258; B01J 31/20; B01J 2351/842
See application file for complete search history.

(56) References Cited

U.S. PATENT DOCUMENTS

| | | | |
|---|---|---|---|
| 8,722,946 B2 | 5/2014 | Close et al. | |
| 8,835,702 B2 | 9/2014 | Close et al. | |
| 8,912,372 B2 | 12/2014 | Wilson et al. | |
| 2004/0225166 A1 | 11/2004 | Wilson et al. | |

OTHER PUBLICATIONS

Asscher, M and Vofsi, D., Chlorine Activation by Redox Transfer. Part II. The Addition of Carbon Tetrahloride to Olefins, 1963, p. 1887-1896.

Freidlina, Chukovskaya, and Englin, A New Type Of Chain Transfer In Radical Telomerization Using An "Intermediary," Doklady Akademii Nauk USSR, Reports of the Academy of Sciences USSR, 1964. vol. 159, No. 6, p. 1346-1349 (Including machine translation).

Freidlina, Grigor'ev, and ENGLIN, Some Characteristics of Telomerization of Propylene and Ethylene with CCl4, Initiated by Iron Pentacarbonyl, 1973, Bull. Acad. Sci. USSR 22 (2) 323-327.

(Continued)

*Primary Examiner* — Jafar F Parsa
(74) *Attorney, Agent, or Firm* — Edel Patents LLC; John B. Edel

(57) ABSTRACT

Chemical processes are disclosed that react iron tetracarbonyl dichloride with an alkyl phosphate producing carbon monoxide and a compound represented by the formula $FeCl_2$—$(O\!\!=\!\!P(OR)_3)_n$ where n is an integer. Simultaneously or subsequently an alkene with carbon tetrachloride may be reacted in the presence of the compound represented by the formula $FeCl_2$—$(O\!\!=\!\!P(OR)_3)_n$ where n is an integer to produce a chlorinated hydrocarbon.

18 Claims, 1 Drawing Sheet

(56) References Cited

OTHER PUBLICATIONS

Tararov, Savel'eva, Struchkov, Pisarevskii, Raevskii, and Belokon, On the Mechanisim of the Fe(CO) 5-Catalyzed Kharasch Reaction 1. Stereochemistry of addition of BrCCl3 to (R)-3-(E)-cinnamoyl-4-phenyloxazolidin-2-one, (R)-3-(E)-acryloyl-4-phenyloxazolidin-2-one, and their pi-complexes with Fe(CO)4, Mar. 1996, Russian Chemical Bulletin, vol. 45, No. 3, p. 600-609.

Asscher and Vofsi, Redox Transfer. Part V. Elementary Steps. The Oxidation of Ferrous and Cuprous Chloride by Carbon Tetrachloride, 1968, Phys. Org., p. 947-952.

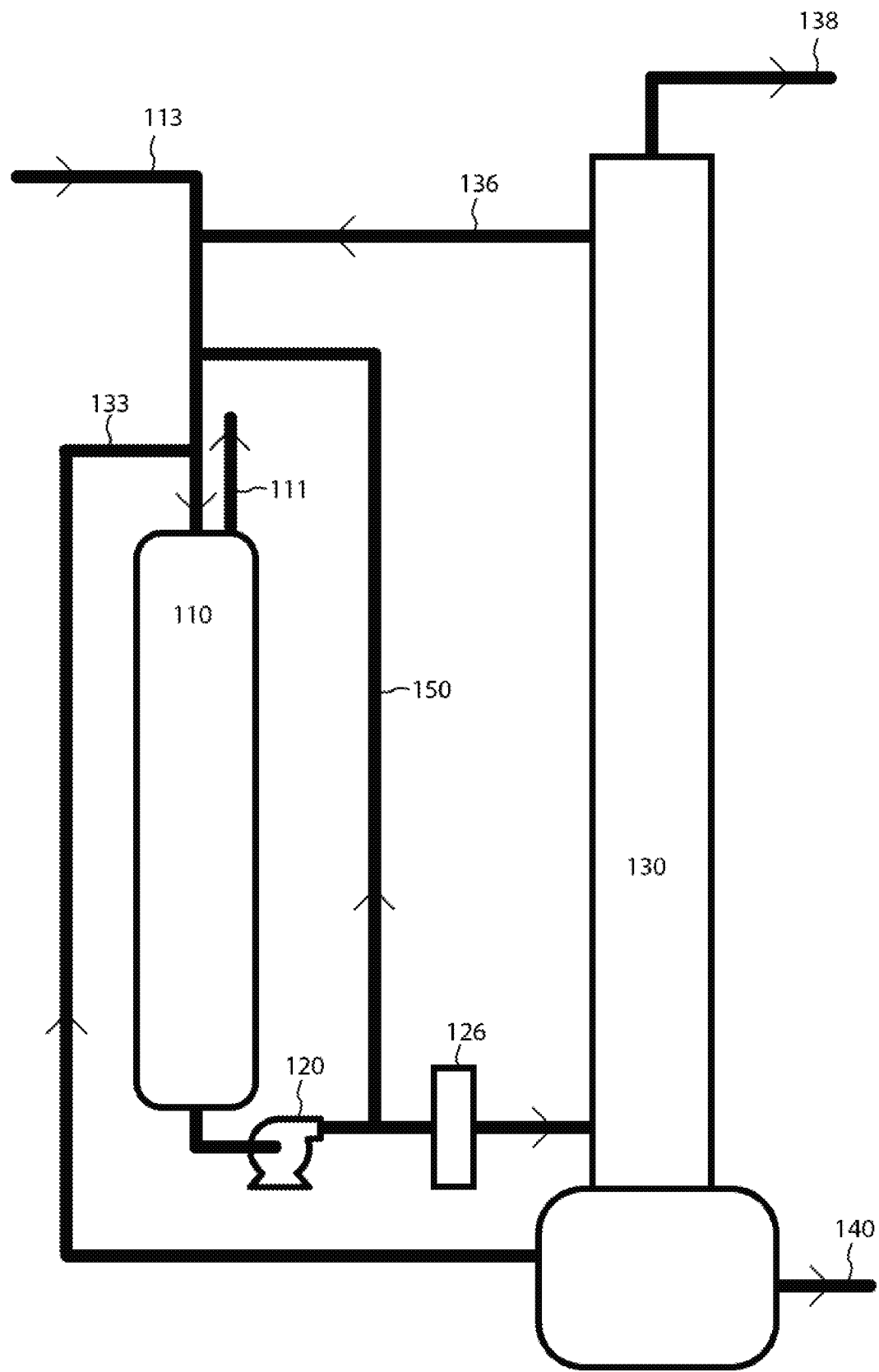

IRON SALT CATALYST REGENERATION

Iron salt catalyzed Kharasch coupling reactions and catalyst regeneration techniques disclosed herein may be used to extend industrial runtime and reactivate catalytic materials. Iron salt catalyzed Kharasch coupling reactions described herein may be used in the preparation of chlorinated compounds.

BRIEF DESCRIPTION OF DRAWINGS

FIG. 1 depicts process equipment from an example iron salt catalyzed Kharasch coupling reaction.

DETAILED DESCRIPTION

FIG. 1 depicts process equipment compatible with the methods described herein. Feedline 113 may be used to provide $CCl_4$, ethylene, and iron pentacarbonyl to reactor 110 which may be initially packed with iron metal and may have a vent line 111 for the removal of CO. Pump 120 allows recirculation through recirculation line 150 and supplies distillation equipment 130. Distillation equipment 130 may recycle iron containing compounds through recycle line 133. Distillation equipment 130 may recycle $CCl_4$ through recycle line 136. The gas and vapor discharge 138 may remove carbon monoxide, HCl gas, and other similarly light components. Product bottoms 140 may include $Cl_3C$—$CH_2$—$CH_2Cl$ and certain iron compounds. Filter 126 is an optional component that may be used to capture particulates.

Certain reactions described herein may produce hydrochlorocarbon chemicals. Certain reactions described herein may be characterized herein as iron salt catalyzed Kharasch coupling reactions.

By adding a liquid source of iron such as iron pentacarbonyl, catalytic iron salts may be reactivated in the system in a manner that is more practical than adding solid forms of metallic iron.

As that phrase is used herein "Kharasch catalytic iron compounds" represent those iron compounds having catalytic properties relative to the reaction:

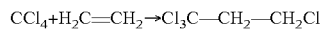
$$CCl_4 + H_2C{=}CH_2 \rightarrow Cl_3C\text{—}CH_2\text{—}CH_2Cl$$

Kharasch catalytic iron compounds may for example be a $Fe(II)$—$(O{=}P(OR)_3)_n$ complex. Other $Fe(II)$ complexes may also be Kharasch catalytic iron compounds if they exhibit catalytic activity relative to the above reaction. In evaluating whether a compound is sufficiently catalytic to be evaluated as a Kharasch catalytic iron compound the compound must have catalytic activity sufficient to produce a reaction rate of at least one tenth the reaction rate produced by the $FeCl_2$—$(O{=}P(OBu)_3)_2$ complex in Experimental Example 3 under similar conditions.

The techniques described herein may be used in continuous reactor, batch operations and semi-batch operations. In many cases the techniques described herein may be used to continue iron salt catalyzed Kharasch coupling reactions after an initial charge of Fe(0) metal has been depleted. The use of iron pentacarbonyl or its equivalents may eliminate or greatly reduce the need to stop operations and open a reactor for the purpose of replacing a spent iron metal Fe(0) catalyst. Economic and environmental advantages may be achieved through increased operation time and reduction of releases associated with catalyst replacement.

Hydrochlorocarbons, hydrochlorofluorocarbons and hydrofluorocarbons may be prepared using the techniques described herein. Further, the techniques described herein may be used in the preparation of chlorocarbons, chlorofluorocarbons and fluorocarbons.

Chlorocarbons and hydrochlorocarbons are, in themselves, useful chemicals. For example, carbon tetrachloride and tetrachloroethene (perchloroethylene) are useful solvents. 1,1,1,-trichloroethane is a useful solvent and chloroethene (vinyl chloride) is a useful monomer for the manufacture of plastics. Chlorocarbons and hydrochlorocarbons are also useful as chemical precursors for the manufacture of chlorofluorcarbons, hydrochlorofluorocarbons, hydrofluorocarbons and fluorocarbons. For example, 1,1,1-trichloroethane can be converted into 1,1,1-trifluoroethane, a propellant and refrigerant. Similarly, 1,1,1,2-tetrachloroethane can be converted to 1,1,1,2-tetrafluoroethane, also a useful refrigerant. Because of their ozone depleting properties, the use of chlorocarbons and chlorofluorocarbons is much less prevalent, with hydrochlorofluorocarbons and hydrofluorocarbons constituting the bulk of useful compounds of this class. Improvements in the preparation of hydrochlorocarbons, hydrochlorofluorocarbons, and hydrofluorocarbons is described herein, but the improvement is equally applicable to the manufacture of chlorocarbons, chlorofluorocarbons and fluorocarbons. These alternate examples may be prepared by selecting compounds with the appropriate substitution and such reaction variations should be considered within the scope of example reactions that may be improved by the present disclosure.

Higher molecular weight hydrochlorocarbons, hydrochlorofluorocarbons, and hydrofluorocarbons may be prepared by coupling a one-or-more carbon fragment with a two-or-more carbon fragment using the techniques described herein in conjunction with other known techniques such as described in *J. Am. Chem. Soc.* 69, 1100-1104 and 1105-1110 (1947).

Compounds of 3 or more carbons and at least 3 chlorine atoms that may be produced by iron salt catalyzed Kharasch coupling reactions, including $Cl_3C$—$CH_2$—$CH_2Cl$ and $Cl_3C$—$CH_2$—$CHCl_2$, may be produced by the reactions and methods disclosed herein.

For example, iron salt catalyzed Kharasch coupling reactions may be used with the techniques described herein in the following reaction to produce 1,1,1,3-tetrachloropropane:

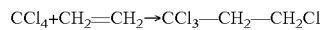
$$CCl_4 + CH_2{=}CH_2 \rightarrow CCl_3\text{—}CH_2\text{—}CH_2Cl$$

The hydrogens on the ethylene may be substituted by other chemical groups such as chlorine, fluorine, and alkyl groups such as methyl-, ethyl-, nitrile, carboxylate-, etc. In addition, one of the chlorines on the carbon tetrachloride may be substituted by another group, such as hydrogen, halogen, alkyl (methyl-, ethyl-, etc.), nitrile and carboxylate groups. Thus, carbon chains (backbones) of more than three carbons may be prepared. An example iron based catalytic reaction may proceed as follows:

$$CCl_4 + FeCl_2 \rightarrow \cdot CCl_3 + FeCl_3 \qquad \text{(Initiation)}$$

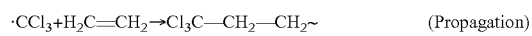
$$\cdot CCl_3 + H_2C{=}CH_2 \rightarrow Cl_3C\text{—}CH_2\text{—}CH_2\cdot \qquad \text{(Propagation)}$$

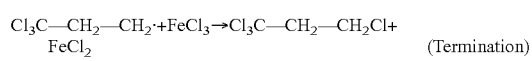
$$Cl_3C\text{—}CH_2\text{—}CH_2\cdot + FeCl_3 \rightarrow Cl_3C\text{—}CH_2\text{—}CH_2Cl + FeCl_2 \qquad \text{(Termination)}$$

Ferrous chloride, $FeCl_2$ may be produced by loading a reactor with some form of iron metal, Fe(0), such that it reacts with carbon tetrachloride to generate $FeCl_2$ in situ.

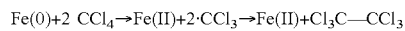
$$Fe(0) + 2\ CCl_4 \rightarrow Fe(II) + 2\cdot CCl_3 \rightarrow Fe(II) + Cl_3C\text{—}CCl_3$$

The use of Fe(0) metal may be further advantageous. During the Initiation step of the reaction, Fe(II) is converted to Fe(III). In the Termination step, the Fe(III) is converted back to Fe(II) which makes the reaction catalytic. There are some side reactions that prevent Fe(III) from converting back to Fe(II) and the Fe(III) accumulates to the detriment of the reaction rate. However, the Fe(0) metal in the reactor is capable of reducing the Fe(III) back to Fe(II) thus keeping the reaction going.

Neither the iron metal Fe(0) nor the iron salts are very soluble in the reaction system nor are they particularly active as catalysts. The coupling reaction is aided by a solubilizing component, often called a co-catalyst or promoter, to be included in the reaction mixture. The co-catalyst promotes the conversion of the iron metal Fe(0) to the iron chloride salt as well as solubilizes the iron chloride salt into the carbon tetrachloride solvent. Such co-catalysts can be amines, nitriles and phosphorus containing compounds such as phosphites and phosphates.

Phosphates such as trialkyl phosphates, $(RO)_3P=O$, may be used. Triethyl phosphate and tributyl phosphate may be used as the phosphates. In such cases, the active catalyst takes the form of an $Fe(II)-(O=P(OR)_3)_n$ complex. More than one phosphate may be involved in the complex depending on the amount of phosphate used.

Fe(0) metal initially loaded into the reactor may be in a wide variety of known forms including iron particles, iron powder, cast iron, wrought iron, and iron wire. Example compositions include carbon steel, mild steel, pure iron, soft iron, ferrosilicon steel, and alloys containing iron such as stainless steel.

Fe(0) metal may be preloaded into the reactor for conversion into Fe(II). An initial charge of co-catalyst trialkyl phosphate may then be injected into the reactor. Once a useful concentration of $Fe(II)-(O=P(OR)_3)_n$ complex has accumulated, the alkene may then be injected continuously into the reactor. Product may then be removed at the rate at which it is produced. Fresh carbon tetrachloride may be continuously introduced into the reactor to replace that which is consumed in the process. The co-catalyst may be dissolved in this carbon tetrachloride stream so that it may also be continuously introduced into the reactor, or it may be injected independently. The reaction may thus be run continuously, constantly introducing carbon tetrachloride, co-catalyst and alkene and constantly withdrawing product. Along with the product, a dissolved mixture of $Fe(II)-(O=P(OR)_3)_n$ complex and $Fe(III)-(O=P(OR)_3)_n$ complex is withdrawn from the reactor and may be recycled to some extent to the reactor after separation from the product. The separation process may be by distillation.

Fe(0) as used herein generally refers to the iron compositions containing iron having an oxidation state of zero such as iron metal. Iron pentacarbonyl is a special instance of Fe(0) described herein. Instances of iron pentacarbonyl are described herein including economically advantageous uses of iron pentacarbonyl. Indications of Fe(0) described herein should be considered as potential opportunities for the use of iron pentacarbonyl. Uses of iron pentacarbonyl as a reducing agent are described herein.

Iron(II) chloride, referred to herein sometimes as $FeCl_2$, refers to both the molecule $FeCl_2$ and depending on the context, including the various reactants involved, may also refer to complexes of $FeCl_2$ including complexes of the general formula $FeCl_2-(O=P(OR)_3)_n$.

Iron(III) chloride, referred to herein sometimes as $FeCl_3$, refers to both the molecule $FeCl_3$ and depending on the context, including the various reactants involved, may also refer to complexes of $FeCl_3$ including complexes of the general formula $FeCl_3-(O=P(OR)_3)_n$.

$Fe(II)-(O=P(OR)_3)_n$ complex describes a range of compounds including the group of compounds characterized as $FeCl_2-(O=P(OR)_3)_n$ complexes in which R represents an alkyl group each instance of which may be a different alkyl group, in which n is a number that is at least one (1), and of which the $FeCl_2-O=P(OBu)_3$ complex is an example. Generally, as used herein, R-groups in the chemical formulas described herein represent alkyl groups each instance of which may be a different alkyl group even if no specific mention is made of whether the R-groups may represent alkyl groups.

$Fe(III)-(O=P(OR)_3)_n$ complex describes a range of compounds including the group of compounds characterized as $FeCl_3-(O=P(OR)_3)_n$ complexes in which R represents an alkyl group each instance of which may be a different alkyl group, in which n is a number that is at least one (1), and of which the $FeCl_3-O=P(OBu)_3$ complex is an example.

A variety of solvents including many phosphate compounds may be capable of contributing to a Kharasch catalytic iron compound or act as co-catalysts. Such co-catalysts can be amines, nitriles and phosphorus containing compounds such as phosphites, phosphates, and phosphoramides. Compounds of the general formula $(RO)_3P=O$ may be particularly useful with $(BuO)_3P=O$ being an example composition. Phosphates that may be used in the processes described herein may include trimethyl phosphate, triethyl phosphate, tripropyl phosphate, and tributyl phosphate. Phosphates of higher molecular weights may also be used. Hexamethylphosphoramide is an example of a phosphate amide that may be used as such a solvent.

Compositions such as represented by the general formula $Y-CCl_3$ wherein Y is selected from hydrogen, halogen, alkyl group, nitrile, and carboxylate may be subjected to the iron salt catalyzed Kharasch coupling reactions with olefins as described herein and $CCl_4$ is an example compound used herein to illustrate the process. Examples using $CCl_4$ herein should also be understood to include examples of a broader group of compounds represented by the formula $Y-CCl_3$.

Alkenes described herein generally represent unsaturated hydrocarbons such as ethylene, but halogen substituted alkenes such as chloroethene (vinyl chloride) may be used. In such situations, the group of halogen substituted alkenes matching the alkene composition or alkene general formula described should be considered as alternate examples that may be used as described.

Iron pentacarbonyl $Fe(CO)_5$ may be used as a liquid substitute for the iron metal, Fe(0), to maintain or regenerate catalyst activity in reaction systems. The introduction of iron pentacarbonyl may eliminate the need to stop the reaction and open the reactor for the replacement of spent catalyst.

In one embodiment, a continuous reactor performing an iron salt catalyzed Kharasch coupling reaction of, for example, carbon tetrachloride and ethylene, having spent its charge of metal Fe(0) may be continuously reactivated by the injection of iron pentacarbonyl $Fe(CO)_5$ Co-solvents such as tributyl phosphate $(BuO)_3P=O$ may be co-injected. The Fe(0) from the $Fe(CO)_5$ reduces inactive Fe(III) back to active Fe(II) catalyst initiator. For example, a $FeCl_3$ complex may be converted back to an active initiating catalytic $FeCl_2$ complex. During this process, the Fe(0) of $Fe(CO)_5$ may be oxidized to Fe(II) and the CO molecules are shed according to the following reaction:

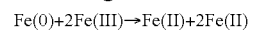

or more specifically,

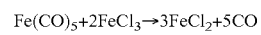

The FeCl$_3$ is present in the form of a co-solvent complex having the general formula FeCl$_3$—(O=P(OR)$_3$)$_n$ and the regenerated FeCl$_2$ is in the form of a co-solvent complex having the general formula FeCl$_2$—(O=P(OR)$_3$)$_n$. To maintain a high level of solubility, the molecule of FeCl$_2$ that is generated from the Fe(CO)$_5$ may be solvated with additional tributyl phosphate.

Fe(CO)$_5$ may undergo a partial or complete ligand exchange of co-solvent for CO. In the case of tributyl phosphate, the initial reaction, where CO is off-gassed may be:

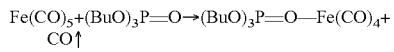

By the time the Fe(CO)$_5$ is converted to FeCl$_2$, all the CO ligands are released. This reaction is demonstrated by the quantitative evolution of CO in the Example reactions described below.

In one embodiment of a spent iron salt catalyzed Kharasch coupling reaction, ½ molar equivalent of Fe(CO)$_5$ is injected for every equivalent of FeCl$_3$ that is desired to be reduced to FeCl$_2$. It is not necessary to allow the coupling catalyst to become completely spent. Iron pentacarbonyl, Fe(CO)$_5$, may be continuously injected at a rate that approximates the rate at which the catalyst is deactivating such that the catalyst maintains a constant level of activity. In certain cases, the injection of Fe(CO)$_5$ may begin when the supply of solid Fe(0) in the reactor is nearing depletion. In other cases, the injection of Fe(CO)$_5$ may be provided over the course of the operations not waiting for the depletion of Fe(0) metal. Fe(CO)$_5$ may, for example, be added when the reaction rate falls below a predetermined threshold reaction rate.

Iron pentacarbonyl may be used in an economically effective way by coupling its use with that of one of the several forms of Fe(0) such as iron filings or wire. Such use may proceed by initially including a substantial charge of solid Fe(0) in a reactor and allowing significant consumption of the solid Fe(0) either prior to the introduction of iron pentacarbonyl or during the introduction of iron pentacarbonyl. In the context of the reactions described herein, a portion of the iron pentacarbonyl supplied to the reactor may be supplied to the reactor after at least half of the available solid Fe(0) in the reactor has been consumed. As that phrase is used herein "native consumable Fe(0) metal" designates metallic iron located in a reactor as a reagent having an oxidation state of zero and having a concentration of at least 10 grams per liter of reactor volume.

In a related embodiment, the off-gassed CO may be continuously removed from the system as it is formed. Purification of the chlorocarbon product along with potential recovery of the catalyst may be achieved in a distillation column. The off-gassed CO may be removed from the head space of the reactor and/or by one or more distillation columns, being taken off in the "non-condensables" stream which may also carry HCl gas and the like.

As described in the reactions herein, Fe(CO)$_5$ does not function directly as a catalyst. Rather it is a material input that ultimately functions as a reducing agent to regenerate spent catalyst, that is convert Fe(III) back to Fe(II).

While Fe(CO)$_5$ may be more expensive than Fe(0) metal it operates simultaneously to regenerate Fe(III) into active catalyst and in the process contributes to the creation of new active catalyst.

Other carbonyls of Fe(0) exist and may be used for potential catalyst regeneration in the processes described herein. Fe$_2$(CO)$_9$ and Fe$_3$(CO)$_{12}$ have potential for such use. Both Fe$_2$(CO)$_9$ and Fe$_3$(CO)$_{12}$ are sparingly soluble in most organic solvents, so they may be used as a source of Fe(0) using the techniques described herein including for example in solutions of CCl$_4$. Examples using Fe(CO)$_5$ described herein should also be understood to include the alternate examples of the above referenced carbonyls of Fe(0).

It should be pointed out for clarity, that in addition to iron pentacarbonyl (aka iron carbonyl), there is a material called carbonyl iron. Carbonyl iron is a finely divided iron powder used to manufacture the iron cores of high frequency magnetic coils for televisions and radios, among other uses. Carbonyl iron is manufactured from iron pentacarbonyl resulting in the similar name. Carbonyl iron plays no role in the reactions described herein.

EXPERIMENTAL EXAMPLES

In the following experimental examples, all chemicals were reagent grade from Aldrich Chemical Corp. Carbon tetrachloride 99.9% and tributyl phosphate 97% were distilled before use. Iron(III) chloride 97% and iron pentacarbonyl 99.9+% were used as received. Ethylene was 99.99%. Reactions were performed in an oven dried and N$_2$ purged 250 mL glass pressure vessel affixed with valves for the introduction of reagents, a pressure gauge and an automatic pressure relief valve set at 100 psig. The vessel was heated in a temperature-controlled oil bath. Stirring was achieved with a Teflon coated magnetic stir bar. Reaction products were washed with 10% HCl, dried with MgSO$_4$ and analyzed on a Varian 3800 Gas Chromatograph with a 60 meter DB-1701 column. Evolved CO gas was captured by water displacement in an inverted 1000 mL graduated cylindrical reservoir.

Experimental Example 1 (Comparative—FeCl$_3$ Alone)

4.87 g (0.03 mol) FeCl$_3$ was charged to a 250 mL glass pressure vessel. 96.5 mL (1.0 mol) CCl$_4$ and 8.2 mL (0.03 mol) (BuO)$_3$P=O were then charged. The system was purged with ethylene gas to displace the N$_2$. The reactor was then warmed to 80° C. and ethylene was charged to 60 psig. The reaction was run for 9 hours under a continuous ethylene pressure of 60 psig. The reactor was cooled, and the remaining pressure released. Gas chromatographic analysis showed the final composition to be 100% CCl$_4$, that is, no reaction had occurred.

Experimental Example 2 (Comparative—Fe(CO)$_5$ Alone)

96.5 mL (1.0 mol) CCl$_4$ and 16.3 mL (0.06 mol) (BuO)$_3$P=O were charged to a 250 mL glass pressure vessel. 3.94 mL (0.03 mol) Fe(CO)$_5$ was injected by syringe and the reaction stirred 15 minutes with no discernable reaction. The system was slowly heated whereupon at about 65° C. the pressure began to rise. When the temperature was 68° C. and the pressure reached 40 psig, the reactor was continuously vented of CO pressure. Venting was continued until CO was no longer evolving whereupon all pressure was vented. A total of about 3420 mL of CO gas was collected. The reactor was then warmed to 80° C. and ethylene was charged to 60 psig. The reaction was run under a continuous ethylene pressure of 60 psig. After 8 hours, the reactor was cooled, and the remaining pressure released. Gas chromatographic analysis showed the final product to be 42.5% 1,1,1,3-tetrachloropropane, 39.3% CCl$_4$, and 9.8% C$_2$Cl$_6$.

Experimental Example 3 (Fe(CO)$_5$ Reactivating FeCl$_3$)

3.24 g (0.02 mol) FeCl$_3$ was charged to a 250 mL glass pressure vessel. 96.5 mL (1.0 mol) CCl$_4$ and 16.3 mL (0.06 mol) (BuO)$_3$P=O were then charged. 1.31 mL (0.01 mol) Fe(CO)$_5$ was injected by syringe and the reaction stirred 15 minutes. Visible CO evolution began immediately. The system was slowly heated. When the temperature was 43° C. and the pressure reached 40 psig, the reactor was continuously vented of CO pressure. Venting was continued until CO was no longer evolving whereupon all pressure was vented. A total of about 1140 mL of CO gas was collected. The reactor was then warmed to 80° C., and ethylene was charged to 60 psig. The reaction was run under a continuous ethylene pressure of 60 psig. After 8 hours, the reactor was cooled, and the remaining pressure released. Gas chromatographic analysis showed the final product to be 44.8% 1,1,1,3-tetrachloropropane, 30.0% CCl$_4$, and 4.4% C$_2$Cl$_6$.

TABLE 1

G.C. Results of Experimental Examples 1-3.

| Experimental Example | Reagents | CCl$_4$ | 1,1,1,3-Tetrachloropropane | C$_2$Cl$_6$ |
|---|---|---|---|---|
| 1 | FeCl$_3$ | 100 | 0 | 0 |
| 2 | Fe(CO)$_5$ | 39.3 | 42.5 | 9.8 |
| 3 | Fe(CO)$_5$ + FeCl$_3$ | 30.0 | 44.8 | 4.4 |

As shown above, both iron pentacarbonyl and iron metal react with the chlorocarbon reagent to become iron in the +2 oxidation state, Fe(II). This results in the consumption of 2 molecules of reagent and also produces an unwanted by-product hexachloroethane Cl$_3$C—CCl$_3$. In a batch reaction, this by-product formation occurs at start-up, while in a continuous reaction, the by-product formation occurs continuously. As long as there is iron in the zero oxidation state Fe(0) converting to iron in the +2 oxidation state Fe(II), by-product formation will occur. Another persistent and similar by-product is tetrachloroethene CCl$_2$=CCl$_2$.

The Kharasch coupling reactions require the use of a co-catalyst or promoter. A frequently used co-catalyst/promoter is a trialkyl phosphate. It has been observed that this compound is degraded to an appreciable extent during the reaction. This degradation is evidenced by the formation of chloroalkane (alkyl chloride). As the examples below will show, this degradation occurs in the presence of zero oxidation state iron Fe(0). The mechanism for this degradation may be as follows:

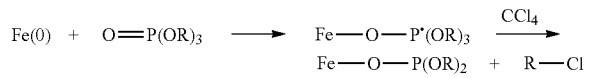

In experimental examples 4-9 below, the amount of hexachloroethane Cl$_3$C—CCl$_3$, the amount of tetrachloroethene CCl$_2$=CCl$_2$, and the amount of chloroalkane (specifically chlorobutane) are used to quantify by-product formation in Kharasch coupling reactions.

Experiments were conducted to determine whether an iron tetracarbonyl halogenide, specifically iron tetracarbonyl dichloride Fe(CO)$_4$Cl$_2$, could be generated within the chemical environment of a Kharasch coupling reaction and then further converted to an active Kharasch coupling catalyst. The reaction may proceed stepwise as follows:

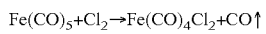

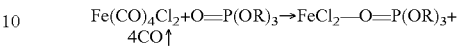

The upward pointing arrow (↑) indicates a gaseous compound that will off-gas and can be vented from the system. Tributyl phosphate, O=P(OBu)$_3$, was used in experiments 4-9 as an exemplary trialkyl phosphate.

A solution of chlorine (Cl$_2$) in carbon tetrachloride (CCl$_4$) may be introduced into a solution of iron pentacarbonyl Fe(CO)$_5$ in carbon tetrachloride to readily form a yellow suspension of Fe(CO)$_4$Cl$_2$. This is accompanied by the evolution of 1 equivalent of carbon monoxide (CO). This suspension remains fluid and stable.

The addition of tributyl phosphate initiates the immediate release of more carbon monoxide (CO) at ambient temperature. This contrasts with the reaction of plain Fe(CO)$_5$ with tributyl phosphate which did not off-gas CO until approximately 74° C. The evolution of CO corresponds to 4 equivalents. Thus, the total CO evolution is 5 equivalents, indicating the formation of the FeCl$_2$—O=P(OBu)$_3$ complex. In contrast to other systems, only a single equivalent of O=P(OBu)$_3$ may be necessary to establish solubility.

The CCl$_4$ solution of the FeCl$_2$—O=P(OBu)$_3$ complex is effective as catalyst in the model reaction CCl$_4$+CH$_2$=CH$_2$→CCl$_3$—CH$_2$—CH$_2$—Cl when exposed to ethylene gas. Thus, an effective catalyst is prepared by the above method.

To determine rigorously whether the use of Fe(CO)$_4$Cl$_2$ generates fewer by-products than either Fe(CO)$_5$ or Fe(0) metal, the series of reactions were performed. In each of these, the catalyst-forming reagents were combined only long enough to form the active catalyst. For reactions utilizing Fe(CO)$_5$, the time frame was complete evolution of 5 equivalents of CO plus 10 minutes at 80° C. For reactions utilizing iron metal Fe(0), the time-frame was that time sufficient to completely dissolve the iron metal at 80° C. In these cases, O=P(OBu)$_3$ an excess of 1 equivalent was necessary for effective dissolution. No ethylene was introduced into these reactions. They were cooled, quenched and analyzed by gas chromatography for impurity content. Reactions were also run in the presence of ferric chloride (FeCl$_3$) to approximate continuous reactor conditions.

In the cases of both Fe(CO)$_5$ and Fe(0) metal, the generation of CCl$_3$—CCl$_3$ was between 10 and 12 percent. Whereas for the case of Fe(CO)$_4$Cl$_2$-generated catalyst, the amount of CCl$_3$—CCl$_3$ was only 3.1 percent. When the reactions of Fe(CO)$_5$ and Fe(0) metal were supplemented with FeCl$_3$, their generation of CCl$_3$—CCl$_3$ only improved to a little more than 5 and 8 percent, respectively. For the case of Fe(CO)$_4$Cl$_2$-generated catalyst supplemented with FeCl$_3$, the amount of CCl$_3$—CCl$_3$ was reduced to a very low 0.5 percent.

Concerning the generation of CCl$_2$=CCl$_2$, in the cases of both Fe(CO)$_5$ and Fe(0) metal, the generation of CCl$_2$=CCl$_2$ was roughly 7 to 8 percent. Whereas for the case of Fe(CO)$_4$Cl$_2$-generated catalyst, the amount of CCl$_2$=CCl$_2$ was only 2.7 percent. When the reactions of Fe(CO) 5 and Fe(0) metal were supplemented with FeCl$_3$, their generation of CCl$_2$=CCl$_2$ only improved to 4.6 and 1.9 percent, respectively. For the case of $Fe(CO)_4Cl_2$-generated catalyst supplemented with $FeCl_3$, the amount of $CCl_2\!\!=\!\!CCl_2$ was reduced to undetectable (0.0%).

The improvement was also evident in the generation of the by-product chlorobutane (Bu-Cl). In the case $Fe(CO)_5$, the generation of Bu-Cl was only 0.4 percent. When the reaction was supplemented with $FeCl_3$, the amount decreased to 0.2 percent. However, for the case of Fe(0) metal, the amount of Bu-Cl was almost 10 percent. When the reaction was supplemented with $FeCl_3$, the generation of Bu-Cl increased to over 12 percent. For the case of $Fe(CO)_4Cl_2$-generated catalyst, the amount of Bu-Cl was less than 0.1 percent. When $Fe(CO)_4Cl_2$-generated catalyst was supplemented with $FeCl_3$, chlorobutane (Bu-Cl) was undetectable (0.0%).

As indicated above, $Fe(CO)_5$ may be introduced into the reaction within the $CCl_4$ feed stream and the $O\!\!=\!\!P(OR)_3$ introduced downstream from that location. In an alternate series of methods, reactions, and reactors consistent with experimental examples 4-9, the $Cl_2$ may be introduced at a location downstream from the Fe(CO) 5 introduction point. Further, $O\!\!=\!\!P(OR)_3$ may be introduced at a location downstream from the $Cl_2$ introduction point.

Various reactor and/or pre-reactor configurations, involving either reactions in process lines or reactions in separate vessels, may be used to carry out the described reactions that have a halogenated carbonyl of iron either as a reactant or a product. This significant variety of process configurations may be used in many variations similar to the process depicted in FIG. 1. These processes may include, but need not include iron metal.

In experimental examples 4-9, chlorine was 99.5% purity and pressure was regulated from a lecture bottle from Aldrich Chemical Corporation. Other chemicals and techniques were as described in experimental examples 1-3.

Experimental Example 4 ($Fe(CO)_4Cl_2$)

50 mL $CCl_4$ was charged to a 100 mL round bottomed flask and cooled in an ice bath. Chlorine gas was bubbled in until 2.13 g (0.03 mol) was dissolved therein. 46.5 mL $CCl_4$ was charged to an evacuated 250 mL glass pressure vessel and cooled in an ice bath with stirring. 3.94 mL (0.03 mol) $Fe(CO)_5$ was injected by syringe. The $Cl_2/CCl_4$ solution was transferred via cannula into the $Fe(CO)_5/CCl_4$ solution. A yellow suspension of $Fe(CO)_4Cl_2$ formed and 693 mL CO evolved over 10 minutes. 8.15 mL (0.03 mol) $(BuO)_3P\!\!=\!\!O$ was then added dropwise. The solution was allowed to warm to room temperature for 10 minutes and then heated to 80° C. with the evolution of an additional 2,780 mL CO. The reaction was then cooled and washed with 10% HCl, then water, and dried with $MgSO_4$. Gas chromatographic analysis showed the final composition to be 94.2% $CCl_4$, <0.1% BuCl, 3.1% $C_2Cl_6$ and 2.7% $CCl_2\!\!=\!\!CCl_2$.

Experimental Example 5 ($Fe(CO)_4Cl_2$ in Presence of $FeCl_3$)

50 mL $CCl_4$ was charged to a 100 mL round bottomed flask and cooled in an ice bath. Chlorine gas was bubbled in until 2.13 g (0.03 mol) was dissolved therein. 9.73 g (0.06 mol) $FeCl_3$ was charged to a 250 mL glass pressure vessel. The flask was then evacuated. 46.5 mL $CCl_4$ was then charged and the flask was cooled in an ice bath with stirring. 3.94 mL (0.03 mol) $Fe(CO)_5$ was then injected by syringe. The $Cl_2/CCl_4$ solution was transferred via cannula into the $Fe(CO)_5/CCl_4$ solution. A yellow suspension of $Fe(CO)_4Cl_2$ formed and 800 mL CO evolved over 10 minutes. 24.5 mL (0.09 mol) $(BuO)_3P\!\!=\!\!O$ was then added dropwise. The solution was stirred for 10 minutes, then allowed to warm to room temperature for 10 minutes and then heated to 80° C. with the evolution of an additional 2,965 mL CO. The reaction was then cooled and washed with 10% HCl, then water, and dried with $MgSO_4$. Gas chromatographic analysis showed the final composition to be 99.5% $CCl_4$, 0.0% BuCl, 0.5% $C_2Cl_6$, and 0.0% $CCl_2\!\!=\!\!CCl_2$.

Experimental Example 6 (Comparative—$Fe(CO)_5$ Alone)

96.5 mL (1.0 mol) $CCl_4$ was charged to a 250 mL glass pressure vessel. 3.94 mL (0.03 mol) $Fe(CO)_5$ and 8.15 mL (0.03 mol) $(BuO)_3P\!\!=\!\!O$ was injected by syringe and the reaction stirred 10 minutes with no discernable reaction. The system was slowly heated whereupon at about 72° C. the first bubbles of CO were observed. When the temperature was 75° C., the reactor was continuously vented of CO pressure. Venting continued until CO was no longer evolving. The reactor was then warmed to 80° C. for 10 minutes. A total of 3,680 mL of CO gas was collected. The reaction was then cooled and washed with 10% HCl, then water, and dried with $MgSO_4$. Gas chromatographic analysis showed the final composition to be 80.6% $CCl_4$, 0.4% BuCl, 10.8% $C_2Cl_6$, and 8.2% $CCl_2\!\!=\!\!CCl_2$.

Experimental Example 7 (Comparative—$Fe(CO)_5$ Reactivating $FeCl_3$)

9.73 g (0.06 mol) $FeCl_3$ was charged to a 250 mL glass pressure vessel. The flask was then evacuated. 96.5 mL (1.0 mol) $CCl_4$ and 3.94 mL (0.03 mol) $Fe(CO)_5$ were then charged. 24.5 mL (0.09 mol) $(BuO)_3P\!\!=\!\!O$ was injected by syringe and the reaction stirred. Visible CO evolution began immediately. The reaction was allowed to warm to room temperature until gas evolution slowed. A total of about 2350 mL of CO gas was collected. The reactor was then heated to 80° C. with the evolution of an additional 1,300 mL CO. The reaction was then cooled and washed with 10% HCl, then water, and dried with $MgSO_4$. Gas chromatographic analysis showed the final composition to be 90.1% $CCl_4$, 0.2% BuCl, 5.2% $C_2Cl_6$, and 24.6% $CCl_2\!\!=\!\!CCl_2$.
Experimental Example 8 (Comparative—Fe(0) Metal)

1.68 g (0.03 mol) of fresh iron filings was charged to a 250 mL glass pressure vessel. The flask was then evacuated. 96.5 mL (1.0 mol) $CCl_4$ and 16.3 mL (0.06 mol) $(BuO)_3P\!\!=\!\!O$ were then charged, and the reaction stirred. The reactor was then heated to 80° C. until all the iron metal was dissolved (2 hrs). The reaction was then cooled and washed with 10% HCl, then water, and dried with $MgSO_4$. Gas chromatographic analysis showed the final composition to be 71.8% $CCl_4$, 9.9% BuCl, 11.5% $C_2Cl_6$, and 6.8% $CCl_2\!\!=\!\!CCl_2$.

Experimental Example 9 (Comparative—Fe(0) Metal Reactivating $FeCl_3$)

1.68 g (0.03 mol) of fresh iron filings and 9.73 g (0.06 mol) $FeCl_3$ were charged to a 250 mL glass pressure vessel. The flask was then evacuated. 96.5 mL (1.0 mol) $CCl_4$ and 49.0 mL (0.18 mol) $(BuO)_3P\!\!=\!\!O$ were then charged. The reactor was then heated to 80° C. until all the iron metal was dissolved (1.5 hrs). The reaction was then cooled and washed with 10% HCl, then water, and dried with $MgSO_4$.

Gas chromatographic analysis showed the final composition to be 77.5% $CCl_4$, 12.4% BuCl, 8.2% $C_2Cl_6$, and 1.9% $CCl_2=CCl_2$.

TABLE 2

G.C. Results of Experimental Examples 4-9

| Experimental Example | Reagents | Chloro-butane | By-products $CCl_3-CCl_3$ | $CCl_2=CCl_2$ |
|---|---|---|---|---|
| 4 | $Fe(CO)_4Cl_2$ | <0.1 | 3.1 | 2.7 |
| 5 | $Fe(CO)_4Cl_2$ + $FeCl_3$ | 0.0 | 0.5 | 0.0 |
| 6 | $Fe(CO)_5$ | 0.4 | 10.8 | 8.2 |
| 7 | $Fe(CO)_5$ + $FeCl_3$ | 0.2 | 5.2 | 4.6 |
| 8 | Fe(0) Metal | 9.9 | 11.5 | 6.8 |
| 9 | Fe(0) Metal + $FeCl_3$ | 12.4 | 8.2 | 1.9 |

Test results indicated that iron tetracarbonyl halogenide, specifically iron tetracarbonyl dichloride $Fe(CO)_4Cl_2$, could be used in a manner similar to iron pentacarbonyl allowing both introduction as a liquid and generation of an active Kharasch catalyst.

Chemical processes described herein may, for example, comprise reacting a reagent of the general formula $Y-CCl_3$ with an alkene in a reactor thereby producing a halogenated hydrocarbon; wherein iron pentacarbonyl is present during the reacting of the reagent of the general formula $Y-CCl_3$ with an alkene; wherein a compound selected from $FeCl_3$ and a $FeCl_3$ complex is removed from the reactor, subjected to separation, and returned to the reactor; wherein the reagent of the general formula $Y-CCl_3$ is added to the reactor during the reacting of the reagent of the general formula $Y-CCl_3$ with the alkene; wherein the iron pentacarbonyl is added to the reactor during the reacting of the reagent of the general formula $Y-CCl_3$ with the alkene; and wherein Y is selected from hydrogen, halogen, alkyl group, nitrile, and carboxylate. In a related example, a phosphate compound may be added to the reactor during the reacting of the reagent of the general formula $Y-CCl_3$ with the alkene. In a related example, the reagent of the general formula $Y-CCl_3$ is $CCl_4$. In a related example, the halogenated hydrocarbon may be a hydrochlorocarbon.

Chemical processes described herein may, for example, comprise loading a reactor with a quantity of Fe(0) metal; supplying $CCl_4$ to the reactor; supplying a phosphate compound to the reactor; supplying an alkene to the reactor; and supplying a carbonyl of Fe(0) to the reactor; wherein a chemical reaction in the reactor produces a halogenated hydrocarbon. In a related example, a portion of the carbonyl of Fe(0) supplied to the reactor may be supplied to the reactor after greater than half of the quantity of Fe(0) metal has been consumed. In a related example, the phosphate compound may be a trialkyl phosphate. In a related example, the carbonyl of Fe(0) may be iron pentacarbonyl. In a related example, the alkene is selected from ethylene, propylene, butylene, chloroethylene, 1,1-dichloroethylene, 1,2-dichloroethylene, trichloroethylene, tetrachloroethylene, fluoroethylene, 1,1-difluoroethylene, 1,2-difluoroethylene, trifluoroethylene, tetrafluoroethylene, 1-chloro-1-fluoroethylene, 1-chloro-2-fluoroethylene, 1,1-dichloro-2-fluoroethylene, 1,2-dichloro-1-fluoroethylene, 1,1,2-trichloro-2-fluoroethylene, 1-chloro-1,2-difluoroethylene, 1-chloro-2,2-difluoroethylene, and 1-chloro-1,2,2-trifluoroethylene. In a related example, related other mixed chlorofluoroethylenes may be used. In a related example, the chemical reaction occurs in the presence of a Kharasch catalytic iron compound.

Chemical processes described herein may, for example, comprise conducting an iron salt catalyzed Kharasch coupling reaction; wherein the iron salt catalyzed Kharasch coupling reaction occurs in the presence of iron pentacarbonyl; wherein iron atoms from the iron pentacarbonyl are oxidized during the iron salt catalyzed Kharasch coupling reaction; wherein iron atoms from a compound selected from $FeCl_3$ and an $FeCl_3$ complex are reduced during the iron salt catalyzed Kharasch coupling reaction; and wherein the iron salt catalyzed Kharasch coupling reaction occurs in the presence of a native consumable Fe(0) metal. In a related example, the iron salt catalyzed Kharasch coupling reaction may occur in the presence of a Kharasch catalytic iron compound. In a related example, the iron salt catalyzed Kharasch coupling reaction may occur in the presence of a phosphate compound. In a related example, the iron salt catalyzed Kharasch coupling reaction may occur in the presence of a trialkyl phosphate. In a related example, the iron salt catalyzed Kharasch coupling reaction may occur in the presence of a reaction of the iron pentacarbonyl with the compound selected from $FeCl_3$ and an $FeCl_3$ complex.

Chemical reactors described herein may, for example, comprise a vessel; a quantity of iron carbonyl within the vessel; a quantity of native consumable Fe(0) metal within the vessel; a quantity of $CCl_4$ within the vessel; a quantity of a $FeX_2-(O=P(OR)_3)_n$ complex within the vessel; a quantity of $FeX_3-(O=P(OR)_3)_n$ complex within the vessel; a quantity of alkene in the vessel; and a quantity of a halogenated hydrocarbon having at least three carbons within the vessel; wherein R is an alkyl group each instance of which may be a different alkyl group; wherein X is a halogen, wherein Y is selected from hydrogen, halogen, alkyl group, nitrile, and carboxylate; and wherein n is a positive number. In a related example, the iron carbonyl may be iron pentacarbonyl. In a related example, n may be selected from 1 and 2.

Chemical processes described herein may, for example, comprise a first reaction in which a halogenated carbonyl of iron is a reactant; a second reaction in which a reactant of the general formula $Y-CCl_3$ reacts with an alkene in a reactor thereby producing a halogenated hydrocarbon; such that the second reaction occurs at a time selected from during the first reaction and after the first reaction; carbon monoxide is a product of the first reaction; the reactant of the general formula $Y-CCl_3$ is added to the reactor during the second reaction; Y is selected from hydrogen, halogen, alkyl group, nitrile, and carboxylate; and a compound selected from an Fe(II) complex and an Fe(III) complex is removed from the reactor, subjected to separation, and returned to the reactor. In a related example, a phosphate compound is added to the reactor during the first reaction. In a related example, the reactant of the general formula $Y-CCl_3$ is $CCl_4$. In a related example, the halogenated carbonyl of iron is an iron tetracarbonyl halogenide. In a related example, the halogenated carbonyl of iron is iron tetracarbonyl dichloride. In a related example, the compound selected from the Fe(II) complex and the Fe(III) complex is a compound selected from a halogenated $Fe(II)-(O=P(OR)_3)_n$ complex and a halogenated $Fe(III)-(O=P(OR)_3)_n$ complex where n is an integer. In a related example, the Fe(II) complex is a further product of the first reaction. In a related example, the compound selected from an Fe(II) complex and an Fe(III) complex is $FeCl_2-O=P(OR)_3$.

Chemical processes described herein may, for example, comprise subjecting a carbonyl of iron to at least one chemical reaction thereby creating a Kharasch catalytic iron compound; supplying $CCl_4$ to a reactor; supplying an alkene to the reactor; such that a chemical reaction takes place in the presence of the Kharasch catalytic iron compound; the chemical reaction that takes place in the presence of the Kharasch catalytic iron compound consumes both a portion of the $CCl_4$ and a portion of the alkene; and the chemical reaction that takes place in the presence of the Kharasch catalytic iron compound produces a chlorinated hydrocarbon. In a related example, the Kharasch catalytic iron compound is represented by the formula $FeCl_2$—(O=P$(OR)_3)_n$ where n is an integer. In a related example, the Kharasch catalytic iron compound is represented by the formula $FeCl_2$—O=P$(OR)_3$. In a related example, a trialkyl phosphate is a reactant in the at least one chemical reaction. In a related example, the carbonyl of iron is iron tetracarbonyl dichloride. In a related example, the alkene is selected from ethylene, propylene, butylene, chloroethylene, 1,1-dichloroethylene, 1,2-dichloroethylene, trichloroethylene, tetrachloroethylene, fluoroethylene, 1,1-difluoroethylene, 1,2-difluoroethylene, trifluoroethylene, tetrafluoroethylene, 1-chloro-1-fluoroethylene, 1-chloro-2-fluoroethylene, 1,1-dichloro-2-fluoroethylene, 1,2-dichloro-1-fluoroethylene, 1,1,2-trichloro-2-fluoroethylene, 1-chloro-1,2-difluoroethylene, 1-chloro-2,2-difluoroethylene, and 1-chloro-1,2,2-trifluoroethylene.

Chemical processes described herein may, for example, comprise reacting iron tetracarbonyl dichloride with an alkyl phosphate thereby producing carbon monoxide and a compound represented by the formula $FeCl_2$—(O=P$(OR)_3)_n$ where n is an integer; and reacting an alkene with carbon tetrachloride in the presence of the compound represented by the formula $FeCl_2$—(O=P$(OR)_3)_n$ where n is an integer to produce a chlorinated hydrocarbon. In a related example, the alkyl phosphate is trialkyl phosphate. In a related example, the alkyl phosphate is tributyl phosphate. In a related example, n is 1.

The above-described embodiments have a number of independently useful individual features that have particular utility when used in combination with one another including combinations of features from embodiments described separately. There are, of course, other alternate embodiments which are obvious from the foregoing descriptions, which are intended to be included within the scope of the present application.

The invention claimed is:

1. A chemical process comprising:
   a. a first reaction in which a halogenated carbonyl of iron is a reactant;
   b. a second reaction in which a reactant of the general formula Y—$CCl_3$ reacts with an alkene in a reactor thereby producing a halogenated hydrocarbon;
   c. wherein the second reaction occurs at a time selected from during the first reaction and after the first reaction;
   d. wherein carbon monoxide is a product of the first reaction;
   e. wherein the reactant of the general formula Y—$CCl_3$ is added to the reactor during the second reaction;
   f. wherein Y is selected from hydrogen, halogen, alkyl group, nitrile, and carboxylate; and
   g. wherein a compound selected from an Fe(II) complex and an Fe(III) complex is removed from the reactor, subjected to separation, and returned to the reactor.

2. The chemical process of claim 1 wherein a phosphate compound is added to the reactor during the first reaction.

3. The chemical process of claim 1 wherein the reactant of the general formula Y—$CCl_3$ is $CCl_4$.

4. The chemical process of claim 1 wherein the halogenated carbonyl of iron is an iron tetracarbonyl halogenide.

5. The chemical process of claim 1 wherein the halogenated carbonyl of iron is iron tetracarbonyl dichloride.

6. The chemical process of claim 1 wherein the compound selected from the Fe(II) complex and the Fe(III) complex is a compound selected from a halogenated Fe(II)—(O=P$(OR)_3)_n$ complex and a halogenated Fe(III)-(O=P$(OR)_3)_n$ complex where n is an integer.

7. The chemical process of claim 1 wherein the Fe(II) complex is a further product of the first reaction.

8. The chemical process of claim 1 wherein the compound selected from an Fe(II) complex and an Fe(III) complex is $FeCl_2$—O=P$(OR)_3$.

9. A chemical process comprising:
   a. subjecting a carbonyl of iron to at least one chemical reaction thereby creating a Kharasch catalytic iron compound;
   b. supplying $CCl_4$ to a reactor;
   c. supplying an alkene to the reactor;
   d. wherein a chemical reaction takes place in the presence of the Kharasch catalytic iron compound;
   e. wherein the chemical reaction that takes place in the presence of the Kharasch catalytic iron compound consumes both a portion of the $CCl_4$ and a portion of the alkene; and
   f. wherein the chemical reaction that takes place in the presence of the Kharasch catalytic iron compound produces a chlorinated hydrocarbon.

10. The chemical process of claim 9 wherein the Kharasch catalytic iron compound is represented by the formula $FeCl_2$—(O=P$(OR)_3)_n$ where n is an integer.

11. The chemical process of claim 9 wherein the Kharasch catalytic iron compound is represented by the formula $FeCl_2$—O=P$(OR)_3$.

12. The chemical process of claim 9 wherein a trialkyl phosphate is a reactant in the at least one chemical reaction.

13. The chemical process of claim 9 wherein the carbonyl of iron is iron tetracarbonyl dichloride.

14. The chemical process of claim 9 wherein the alkene is selected from ethylene, propylene, butylene, chloroethylene, 1,1-dichloroethylene, 1,2-dichloroethylene, trichloroethylene, tetrachloroethylene, fluoroethylene, 1,1-difluoroethylene, 1,2-difluoroethylene, trifluoroethylene, tetrafluoroethylene, 1-chloro-1-fluoroethylene, 1-chloro-2-fluoroethylene, 1,1-dichloro-2-fluoroethylene, 1,2-dichloro-1-fluoroethylene, 1,1,2-trichloro-2-fluoroethylene, 1-chloro-1,2-difluoroethylene, 1-chloro-2,2-difluoroethylene, and 1-chloro-1,2,2-trifluoroethylene.

15. A chemical process comprising:
   a. reacting iron tetracarbonyl dichloride with an alkyl phosphate thereby producing carbon monoxide and a compound represented by the formula $FeCl_2$—(O=P$(OR)_3)_n$ where n is an integer; and
   b. reacting an alkene with carbon tetrachloride in the presence of the compound represented by the formula $FeCl_2$—(O=P$(OR)_3)_n$ where n is an integer to produce a chlorinated hydrocarbon.

16. The chemical process of claim 15 wherein the alkyl phosphate is trialkyl phosphate.

17. The chemical process of claim 15 wherein the alkyl phosphate is tributyl phosphate.

18. The chemical process of claim 15 wherein n is 1.

* * * * *